United States Patent
Cha et al.

(10) Patent No.: US 11,814,556 B2
(45) Date of Patent: Nov. 14, 2023

(54) COACERVATE FORMED FROM CATECHOL-SUBSTITUTED ANIONIC POLYMER, ADHESIVE COMPRISING SAME, AND METHOD FOR PRODUCING SAME

(71) Applicants: POSCO, Pohang-si (KR); POSTECH ACADEMY-INDUSTRY FOUNDATION, Pohang-si (KR); NATURE GLUETECH CO., LTD., Seoul (KR)

(72) Inventors: Hyung Joon Cha, Pohang-si (KR); Hyo Jeong Kim, Busan (KR); Bong-Hyuk Choi, Gyeongju-si (KR)

(73) Assignees: POSCO CO., LTD, Pohang-si (KR); POSTECH ACADEMY-INDUSTRY FOUNDATION, Pohang-si (KR); NATURE GLUETECH CO., LTD., Seoul (KR)

( * ) Notice: Subject to any disclaimer, the term of this patent is extended or adjusted under 35 U.S.C. 154(b) by 596 days.

(21) Appl. No.: 16/649,224

(22) PCT Filed: Jul. 10, 2018

(86) PCT No.: PCT/KR2018/007799
§ 371 (c)(1),
(2) Date: Mar. 20, 2020

(87) PCT Pub. No.: WO2019/059504
PCT Pub. Date: Mar. 28, 2019

(65) Prior Publication Data
US 2020/0299556 A1 Sep. 24, 2020

(30) Foreign Application Priority Data
Sep. 20, 2017 (KR) .................. 10-2017-0121382

(51) Int. Cl.
*C09J 189/00* (2006.01)
*C07K 14/435* (2006.01)
*A61L 24/10* (2006.01)

(52) U.S. Cl.
CPC ....... *C09J 189/00* (2013.01); *C07K 14/43504* (2013.01)

(58) Field of Classification Search
CPC ............. C09J 189/00; C07K 14/43504; C07K 14/435; A61L 24/043; A61L 24/10
See application file for complete search history.

(56) References Cited

U.S. PATENT DOCUMENTS

| 2009/0151600 A1 | 6/2009 | Cha |
| 2014/0005356 A1 | 1/2014 | Cha |

FOREIGN PATENT DOCUMENTS

| EP | 2471819 A2 | 7/2012 |
| JP | 2014-177636 A | 9/2014 |
| KR | 10-2006-0134111 A | 12/2006 |
| KR | 10-2011-0021650 A | 3/2011 |
| KR | 10-2012-0013626 A | 2/2012 |
| KR | 10-2013-0010385 A | 1/2013 |
| KR | 10-2014-0002244 A | 1/2014 |
| KR | 10-2014-0027031 A | 3/2014 |
| KR | 10-2016-0113372 A | 9/2016 |
| WO | 2005/092920 A1 | 10/2005 |
| WO | 2006/107183 A1 | 10/2006 |

OTHER PUBLICATIONS

JP 2014177636 English Machine translation, pp. 1-27. Sep. 25, 2014. (Year: 2014).*
Park et al., "Catechol-Functionalized Hyaluronic Acid Hydrogels Enhance Angiogenesis and Osteogenesis of Human Adipose-Derived Stem Cells in Critical Tissue Defects," BioMacromolecules, 2016, 17: 1939-1948. (Year: 2016).*
Kim et al., "Adhesive Catechol-Conjugated Hyaluronic Acid for Biomedical Applications: A Mini Review," Applied Sciences, 2021, 11(21): pp. 1-14, enclosed. (Year: 2021).*
Extended European Search Report dated Sep. 17, 2020 issued in European Patent Application No. 18859597.9.
International Search Report dated Jan. 2, 2019 issued in International Patent Application No. PCT/KR2018/007799 (with English translation).
Yeon Jeong Oh, et al., "Bio-inspired catechol chemistry: a new way to develop a re-moldable and injectable coacervate hydrogel", Chem. Commun., 2012, pp. 11895-11897.
Dong Soo Hwang, et al., "Viscosity and interfacial properties in a mussel-inspired adhesive coacervate", Soft Matter, 2010, pp. 3232-3236.

* cited by examiner

*Primary Examiner* — Julie Ha
(74) *Attorney, Agent, or Firm* — Morgan, Lewis & Bockius LLP (57) ABSTRACT

A coacervate including a catechol-substituted anionic polymer; an adhesive including same; and a method for producing the coacervate are described. More specifically, a coacervate formed by mixing a catechol derivative of a mussel adhesive protein and a catechol-substituted anionic polymer; an adhesive including the coacervate; and a method for producing a coacervate are described. The method includes a step of obtaining a catechol-substituted anionic polymer through catechol substitution of an anionic polymer, and a step of mixing the catechol-substituted anionic polymer and a catechol derivative of a mussel adhesive protein.

7 Claims, 9 Drawing Sheets

FIG.5 mrMAP & Cat-HA (10)
COMPLEX COACERVATE mrMAP & Cat-HA(20)
AGGREGATE

COACERVATE FORMED FROM CATECHOL-SUBSTITUTED ANIONIC POLYMER, ADHESIVE COMPRISING SAME, AND METHOD FOR PRODUCING SAME

CROSS-REFERENCE OF RELATED APPLICATIONS

This application is the U.S. National Phase under 35 U.S.C. § 371 of International Patent Application No. PCT/KR2018/007799, filed on Jul. 10, 2018, which in turn claims the benefit of Korean Application No. 10-2017-0121382, filed on Sep. 20, 2017, the entire disclosures of which applications are incorporated by reference herein.

TECHNICAL FIELD

The present invention relates to a coacervate formed from a catechol-substituted anionic polymer, an adhesive comprising the same, and a method for producing the same, more specifically, to a coacervate having excellent adhesion strength and containing a mussel adhesive protein and hyaluronic acid conjugated with catechol.

BACKGROUND ART

Recently, as demand for non-invasive or less-invasive testing and treatment has gradually increased, a need for development of an effective tissue adhesive has been continuously raised. A conventional suturing method using sutures is widely used in many surgical procedures but has a limitation that it cannot be used for suturing organs such as the bladder and heart, which repeatedly contract and expand, and the brain or a lung, which can be easily damaged by physical pressure. Accordingly, research and development of adhesives that can replace or supplement the use of such sutures have actively been conducted. Thus-far developed synthetic adhesives, however, have high histotoxicity and physical properties after crosslinking are significantly different from those of an actual tissue, which may cause tissue damage.

In contrast, naturally derived protein-based adhesives have superior biocompatibility, but uses thereof are very limited due to significantly low tissue adhesion strength. Meanwhile, even in the case of a tissue adhesive formed of a high biocompatible synthetic polymer, such as polyethylene glycol (PEG), there is a limit that a tissue in vivo does not have sufficient adhesion strength and mechanical properties.

In order to solve this problem, in marine environments, adhesive proteins secreted by mussels have been mass-produced through genetic recombination with excellent adhesion strength in the marine environment, considering mussels with excellent adhesion strength. There have also been attempts to develop adhesives that do not disintegrate, even in water, through the formulation of complex coacervation. Such underwater adhesives showed excellent water resistance and adhesion strength in laboratory tests, but have disadvantages in that they require a significantly long time to reach adhesion strength or mechanical properties required in actual animal experiments or clinical trials.

In order to effectively use such protein adhesives in actual clinical practice, it is necessary to have sufficient adhesion strength and mechanical properties within 5 minutes, so that uncrosslinked adhesives can be washed away by body fluids or flow away without being fixed. In addition, if the treated adhesive is very different from the properties or properties of the tissue to which it is applied, it may cause damage to the tissue and a reduction of the adhesion strength effect due to the difference in mechanical strength between the adhesive and the tissue.

Therefore, there is an urgent need for the development of tissue-specific tissue adhesives that can exhibit a variety of mechanical properties depending on the use while showing faster and better adhesion strength in tissue in vivo.

(Patent document 1) KR 10-2015-0037580

DISCLOSURE

Technical Problem

An aspect of the present invention is to provide a coacervate exhibiting rapid and excellent adhesion strength.

Another aspect of the present invention is to provide an adhesive containing coacervate.

Still another aspect of the present invention is to provide a method for producing such a coacervate.

Technical Solution

According to an aspect of the present invention, a coacervate formed by mixing a catechol derivative of a mussel adhesive protein and a catechol-substituted anionic polymer is provided.

According to another aspect, an adhesive containing the coacervate is provided.

According to still another aspect, a method for producing a coacervate is provided, where the method includes obtaining a catechol-substituted anion polymer by substituting an anionic polymer with catechol; and mixing the catechol-substituted anion polymer with a catechol derivative of a mussel adhesive protein.

Advantageous Effects

According to the present invention, catechol can be controlled to be conjugated into hyaluronic acid in different amounts by varying a reaction condition. Thus-synthesized catechol-hyaluronic acid can form a complex coacervate together with a mussel adhesive protein. As described above, the coacervate containing catechol-hyaluronic acid involves faster crosslinking and has superior mechanical properties as compared to an existing adhesive formed of hyaluronic acid, and thus has excellent adhesion strength and closing force. In addition, as hyaluronic acids of various molecular weights are used together with a mussel adhesive protein to produce a mixed coacervate, a tissue adhesive having various mechanical and rheological properties can ultimately be prepared. A novel tissue adhesive having a fast crosslinking time, excellent adhesion strength and various properties is expected to be available in numerous clinical applications in which tissue adhesives are currently difficult to use.

BEST MODE

Hereinafter, the preferred embodiment of the present invention will be described with reference to the accompanying drawings. The present invention may, however, be embodied in many different forms and should not be construed as being limited to the embodiments set forth herein.

According to the present invention, a coacervate, which can be applied as a novel tissue adhesive having a fast crosslinking time, excellent adhesion strength and various properties, is provided.

More specifically, the coacervate of the present invention is formed by mixing a catechol derivative of a mussel adhesive protein and a catechol-substituted anionic polymer.

The mussel adhesive proteins disclosed in KR10-2014-0002244, AW02006/107183, WO2005/092920, or the like may be used for that of the present invention. A detailed production process may be the same as that disclosed in WO2006/107183 and WO2005/092920.

As used herein, a mussel adhesive protein, in which a tyrosine residue is modified to a catechol derivative, is referred to a "modified mussel adhesive protein" or a "catechol derivative of a mussel adhesive protein," and a modification method thereof is not particularly limited.

A mussel adhesive protein, which can be applied hereto, may be a mussel-derived adhesive protein, and may preferably include a mussel adhesive protein derived from *Mytilus edulis, Mytilus galloprovincialis* or *Mytilus coruscus*, or a variant thereof, but is not limited thereto.

The mussel adhesive protein may include a *Mytilus edulis* foot protein (Mefp)-1, Mefp-2, Mefp-3, Mefp-4, Mefp-5, *Mytilus galloprovincialis* foot protein (Mgfp)-1, Mgfp-2, Mgfp-3, Mgfp-4, Mgfp-5, *Mytilus coruscus* foot protein (Mcfp)-1, Mcfp-2, Mcfp-3, Mcfp-4, Mcfp-5, which is derived from said mussel, or a variant thereof, and may preferably include a protein selected from the group consisting of foot protein (fp)-1, fp-2, fp-3, fp-4, fp-5 and fp-6, or a fusion protein to which at least one protein selected from the group is linked, or a variant thereof, but is not limited thereto.

Further, the mussel adhesive protein of the present invention may include all mussel adhesive proteins disclosed in WO2006/107183 and WO2005/092920. Preferably, the mussel adhesive protein may include fusion proteins such as fp-151, fp-131, fp-353, fp-153, fp-351, and the like, but is not limited thereto. In addition, the mussel adhesive protein may include a polypeptide, in which 1 to 12 or more decapeptides are linked in tandem, where the decapeptides recur about 80 times in fp-1 is, and may preferably be an fp-1 variant polypeptide in which 12 decapeptides of SEQ ID NO:2 are connected in tandem, but is not limited thereto.

The present inventors developed an fp-151, a novel mussel adhesive protein in which a structure of their previous study, in which 10 repeating amino acids of the fp-1 recur 6 times, is connected to N- and C-termini of fp-5 at a genetic level, and successfully expressed the recombinant mussel adhesive protein in *E. coli*, thereby finding feasibility of mass production thereof and significantly high industrial applicability through simple purification processes (WO2006/107183 and WO2005/092920).

The catechol derivative is a compound containing a dihydroxyl group and is coordinatable with a metal. The catechol derivative is preferably at least one selected from the group consisting of 3,4-dihydroxyphenylalanine (DOPA), DOPA o-quinone, dopamine, norepinephrine, epinephrine, epigallocatechin gallate and derivatives thereof. For example, it is preferable that the catechol derivative be at least one selected from the group consisting of DOPA, DOPA o-quinone, TOPA, TOPA quinone and derivatives thereof.

For example, the catechol derivative of the mussel adhesive protein may have 10% to 100% of a total number of tyrosine residues substituted with a catechol derivative, particularly to DOPA.

The anionic polymer of the present invention may be at least one selected from the group consisting of hyaluronic acid, ferredoxin, polystyrene sulfonic acid, gum arabic, gelatin, albumin, Carbopol, high or low methoxyl pectin, sodium carboxymethyl guar gum, xanthan gum, whey protein, faba bean legumin, carboxymethyl cellulose, alginate, carrageenan, sodium hexametaphosphate, sodium casinate, hemoglobin, heparin and exopolysaccharide B40, and preferably hyaluronic acid.

The anionic polymer may have a molecular weight of 1 kDa to 5000 kDa. Although not limited, the anionic polymer may preferably have a molecular weight selected from the group consisting of 6 kDa to 2000 kDa, more preferably a molecular weight of 10 kDa to 1500 kDa. In the case of a molecular weight below or exceeding said molecular weight, a coacervate may not be formed or may be difficult to be injected through a needle having a small diameter due to increased viscosity. In particular, when hyaluronic acid having a molecular weight of 10 kDa or more is used, the coacervate may be formed more easily. When that having a molecular weight exceeding 1500 kDa is used, the coacervate may be formed, but may be difficult to be injected through a needle having a small diameter due to significantly high viscosity of the formed coacervate. In the case of a tissue adhesive, the adhesive in a liquid form should be able to be injected in vivo before crosslinking, and thus, viscosity thereof needs to be controlled.

Figure 4:
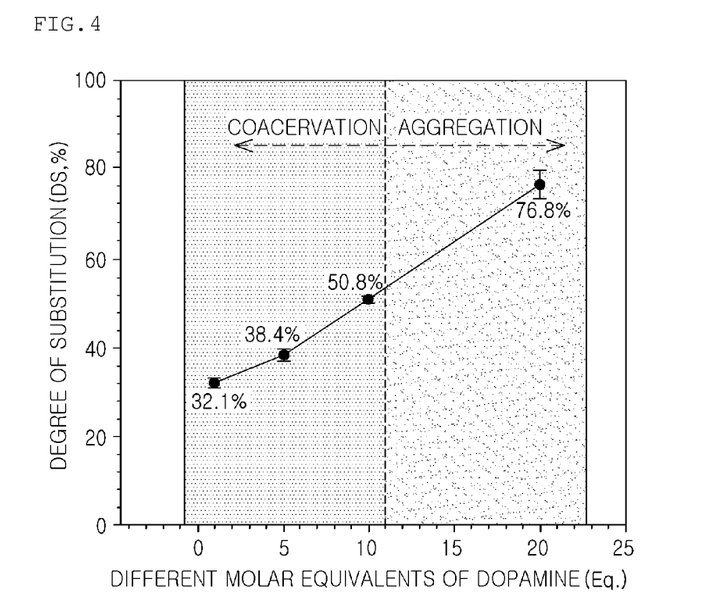
FIG. 4 is a graph illustrating that a degree of substitution of 50% or less results in a complex coacervate and a degree of substitution of 50% or more results in precipitation, considering that the degree of catechol-hyaluronic acid substitution varies according to an equivalent amount of dopamine added to the EDC/NHS reaction.

As used herein, the anionic polymer may preferably have a degree of catechol substitution of 10% to 52%, more preferably 30% to 50%; for example, 35% to 50%. As illustrated in FIG. 4, when the degree of catechol substitution of the anionic polymer exceeds 52%, an anionic residue of the hyaluronic acid, reactive with the mussel adhesive protein, is substituted by catechol, which may result in aggregation and subsequent precipitation instead of formation of coacervate. Further, when the degree of catechol substitution is less than 30%, the coacervate formation may not be an issue but is not preferable in terms of the purpose of the present invention, which is to obtain maximum adhesion strength.

In order to obtain such substitution degree, a concentration of hyaluronic acid in an aqueous solution of hyaluronic acid used in a production process is preferably 0.5 g/L to 10 g/L, more preferably 5 g/L to 10 g/L.

Subsequently, catechol, for example, dopamine hydrochloride, is added in a molar equivalent, equivalent to 1 to 50 times an amount of hyaluronic acid, preferably 10 to 20 times, to the aqueous solution of hyaluronic acid having said concentration. More preferably, 10 equivalents or less is mixed.

A pH is set to preferably be 4 to 5.5, more preferably 4.5 to 5.0, for 1 hour to 48 hours, preferably 24 hours to 48 hours at room temperature.

As used herein, the "coacervate" refers to a type of colloid formed by mixing the catechol derivative of the mussel adhesive protein and the catechol-substituted anionic polymer. That is, the coacervate in the present invention is formed by mixing the catechol derivative of the mussel adhesive protein and the catechol-substituted anionic polymer.

Although not limited thereto, the coacervate may be prepared in an aqueous solvent, more preferably methanol, ethanol, propanol, acetone or an aqueous acetic acid solution, even more preferably aqueous acetic acid solution, far even more preferably 0.1% to 10% aqueous acetic acid solution, most preferably 0.5% to 8% aqueous acetic acid solution.

The coacervate of the present invention may be prepared to additionally contain at least one pharmaceutically acceptable carrier. The pharmaceutically acceptable carrier may be saline, sterile water, Ringer's solution, buffered saline, dextrose solution, maltodextrin solution, glycerol, ethanol, liposome and a mixture of at least one thereof. If necessary, another additive, such as an antioxidant, a buffer solution, a bacteriostatic agent, or the lie, may be added. A diluant, a dispersant, a surfactant, a binder and a lubricant may be additionally added to prepare the coacervate in an injectable formulation, such as an aqueous solution, a suspension, an emulsion, or the like, a pill, a capsule, a granule or a tablet. The carrier may be used in combination with a target organ-specific antibody or another ligand to specifically act on a target organ. Further, an appropriate method in the art or the method disclosed in Remington's reference (Pharmaceutical Science (Recent Edition), Mack Publishing Company, Easton Pa.) may be used to preferably formulate the coacervate according to a disease or an ingredient.

Meanwhile, according to the present invention, an adhesive containing the coacervate of the present invention may be provided, where the adhesive may be a tissue adhesive composition.

For example, the composition containing the coacervate may be delivered in vivo via intravenous, intraperitoneal, intramuscular, subcutaneous, intradermal, nasal, mucosal, inhalation, and oral routes.

A dosage may vary depending on weight, age, gender, medical condition, diet, administration time, administration route and excretion rate of a subject and severity of a disease. A daily dosage may be 0.1 mg/Kg, preferably 0.5 mg/Kg to 10 mg/Kg. The composition may be more preferably administered once a day or divided into multiple doses.

Furthermore, according to the present invention, a method for producing the coacervate is provided.

The method for producing the coacervate of the present invention includes obtaining a catechol-substituted anion polymer by substituting an anionic polymer with catechol and mixing the catechol-substituted anion polymer with a catechol derivative of a mussel adhesive protein.

As previously described, the mixing may be performed in an aqueous solvent, more preferably methanol, ethanol, propanol, acetone and aqueous acetic acid solution, even more preferably aqueous acetic acid solution, far even more preferably 0.1% to 10% aqueous acetic acid solution, most preferably 0.5% to 8% aqueous acetic acid solution.

The mixing of the catechol-substituted anionic polymer and the catechol derivative of the mussel adhesive protein may be performed at pH 2.5 to pH 7.0 at a molecular weight ratio of 1:0.1 to 1.10.

More specifically, when the coacervate is produced in said solvent, an appropriate pH may be preferably 2.5 to 7.0, more preferably 3.0 to 6.0, even more preferably 3.5 to 5.5, although not limited thereto. A pH below or exceeding said pH may result in modification of the polymer and formation of no coacervate.

Although not limited thereto, amounts of the catechol derivative of the mussel adhesive protein and the catechol-substituted anionic polymer added to the solvent may be preferably 1% (w/v) to 100% (w/v), more preferably 30% (w/v) to 70% (w/v), based on a total volume of the solvent.

Although not limited thereto, the coacervate may be formed by mixing the catechol-substituted anion polymer with the catechol derivative of the mussel adhesive protein at a molar ratio of preferably 1:0.1 to 1:10, more preferably 1:0.25 to 1:1.5, even more preferably 1:0.43 to 1:1.5. A mixing ratio lessor exceeding the above may result in ineffective formation of coacervate.

A novel tissue adhesive of the present invention, which is formed by mixing the catechol-substituted anion polymer with the catechol derivative of the mussel adhesive protein to have a faster crosslinking time, excellent adhesion strength and various properties, can be provided, and thus is expected to be used in various clinical trials where tissue adhesives are currently difficult to use.

Hereinbelow, the present invention will be described in more detail with reference to specific exemplary embodiments. The following exemplary embodiments are merely examples to help understanding of the present invention, and the scope of the present invention is not limited thereto.

MODE FOR INVENTION

Examples

1. Production of Hyaluronic Acid to which Catechol is Introduced

Figure 1:
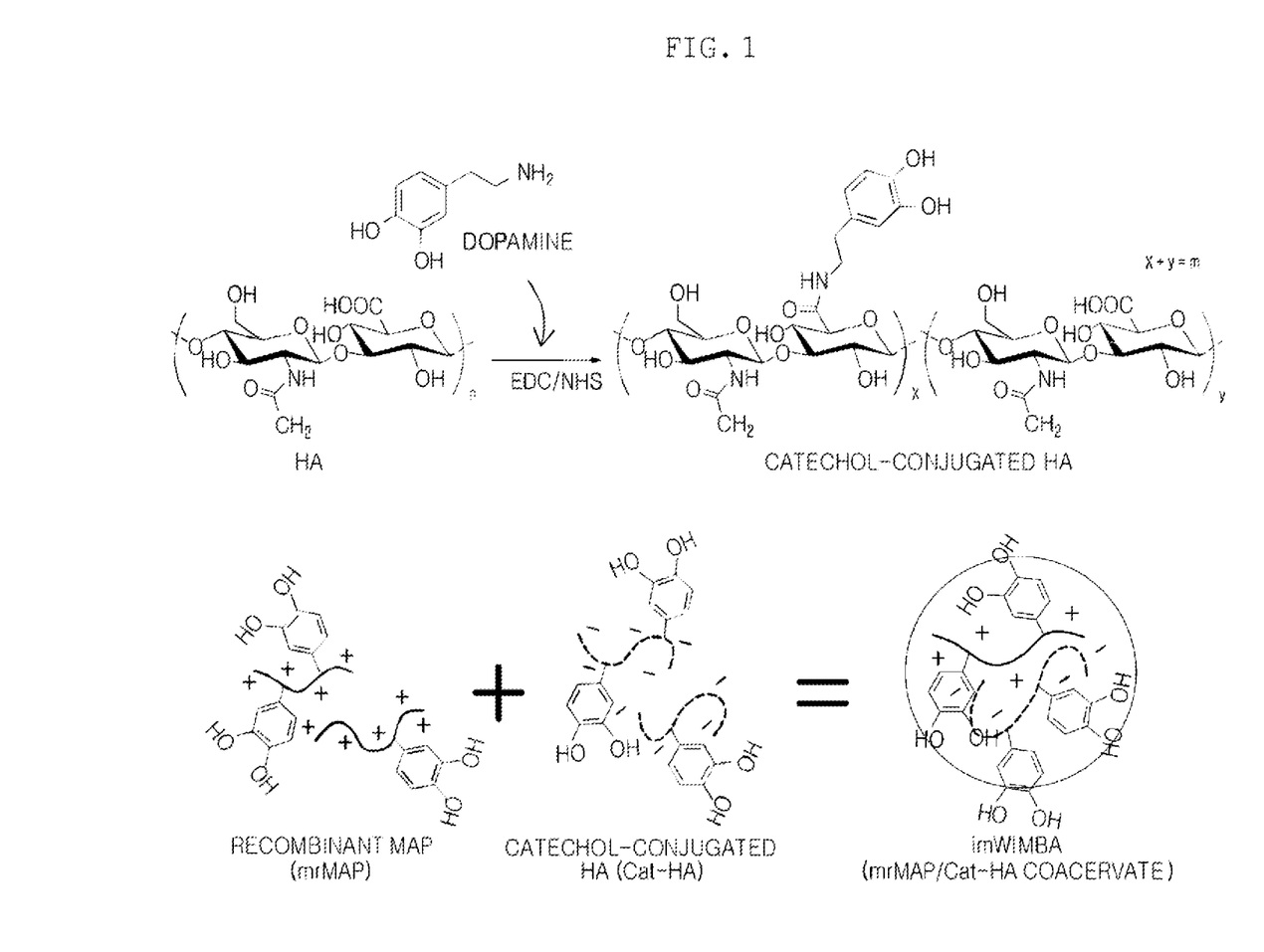
FIG. 1 is a schematic diagram illustrating a formula of an 1-ethyl-3-(3-dimethylaminopropyl) carbodiimide (EDC)/N-hydroxysuccinimide (NHS) reaction to attach dopamine to a carboxyl group and forming a mixed coacervate from a catechol derivative of a mussel adhesive protein and a catechol-hyaluronic acid.

FIG. 1 schematically illustrates a production process of hyaluronic acid in which catechol is conjugated. More specifically, hyaluronic acid is dissolved in water or PBS, where PBS is preferable over water. A molecular weight of the hyaluronic acid is 1 kDa to 5000 kDa and may vary depending on a use thereof. In this experiment, hyaluronic acid having a molecular weight of 10 kDa to 1500 kDa was used.

Figure 2:
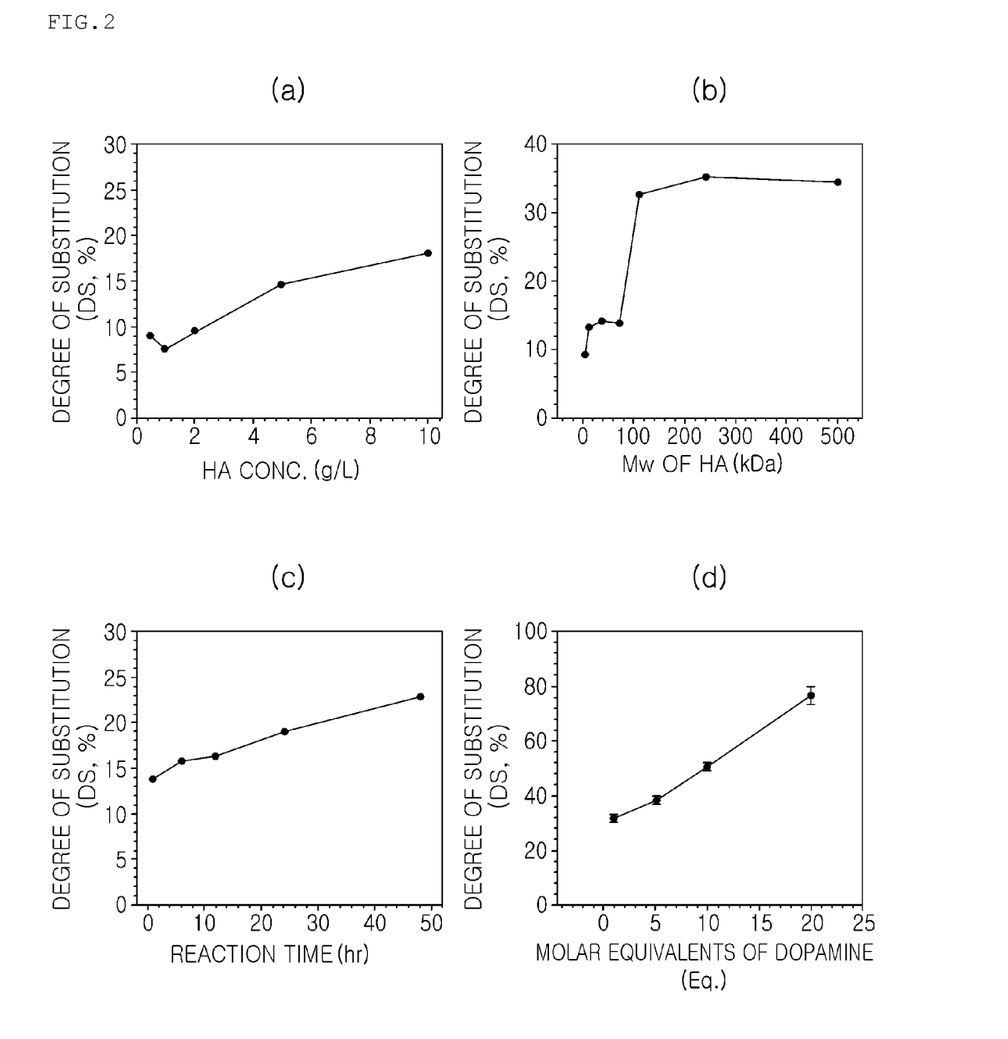
FIG. 2 is a graph illustrating a substitution rate of the catechol-hyaluronic acid according to a reaction concentration, a molecular weight, a reaction time and a molar equivalent of the hyaluronic acid.

A concentration of hyaluronic acid used in a reaction may be 0.5 g/L to 10 g/L. In this experiment, 5 g/L hyaluronic acid was used. Molar equivalents of 1-ethyl-(3,3-dimethyl aminopropyl) carbodimide hydrochloride (EDC) and N-hydroxysuccinimide (NHS) to hyaluronic acid were added in order to a solution in which hyaluronic acid has been dissolved and were subject to continuous mixing. Dopamine hydrochloride was then added in a molar equivalent, equivalent to 1 to 50 times that of hyaluronic acid, is added. In this experiment, 10 times equivalents thereto were added. A pH of thus-mixed solution was set to 4.5 to 5.0, and the solution was allowed to react at room temperature for 24 hours. In this case, a degree of substitution of the catechol-hyaluronic acid is about 48% to 52%. FIG. 2 is a graph illustrating a substitution rate of the catechol-hyaluronic acid according to a reaction concentration, a molecular weight, a reaction time and a molar equivalent of the hyaluronic acid.

2. Production of Coacervate

A mussel adhesive protein fp-151 was produced from *E. coli* by synthesizing a *Mytilus* mussel foot protein type-1 (fp-1) variant consisting of decapeptides (AKPSYPPTYK) 6 times repeating in an amino acid sequence of a mussel adhesive protein fp-1 (Genbank No. Q27409) present in nature and inserting a Mgfp-5 gene (Genbank No. AAS00463) between 2 fp-1 variants. The fp-151 production was performed as disclosed in WO2005/092920, which is incorporated herein by reference in an entirety thereof.

A mushroom tyrosinase (SIGMA) was used to carry out an in vitro enzyme reaction such that the tyrosine residue of the mussel adhesive protein fp-151 was converted to dihydroxyphenylalanine (DOPA). Specifically, a 1.50 mg/mL fp-151 solution and a 100 μm/mL tyrosinase buffer solution (100 mM sodium phosphate, 20 mM boric acid, 25 mM ascorbic acid, pH 6.8) were allowed to react for 1 hour, followed by dialyzing using 1% acetic acid solution. A catechol derivative of a mussel adhesive protein, a cationic recombinant mussel adhesive protein, was thus produced.

The cationic mussel adhesive protein and the anionic catechol-hyaluronic acid prepared in 1. were individually dissolved in an acetate buffer solution at pH 4 followed by mixing the same to produce a coacervate. As the coacervate production is significantly affected by a mole fraction between substances, an optimal condition was to be found for the formation of a largest amount of coacervate. Bradford analysis (Bio-Rad) was employed to measure a concentration of a protein, and catechol-hyaluronic acid were added at various ratios. Using the fact that an amount of thus-formed coacervate is proportional to absorbance, a highest mole fraction exhibiting highest absorbance was measured, and a result thereof is shown in FIG. 3.

Figure 3:
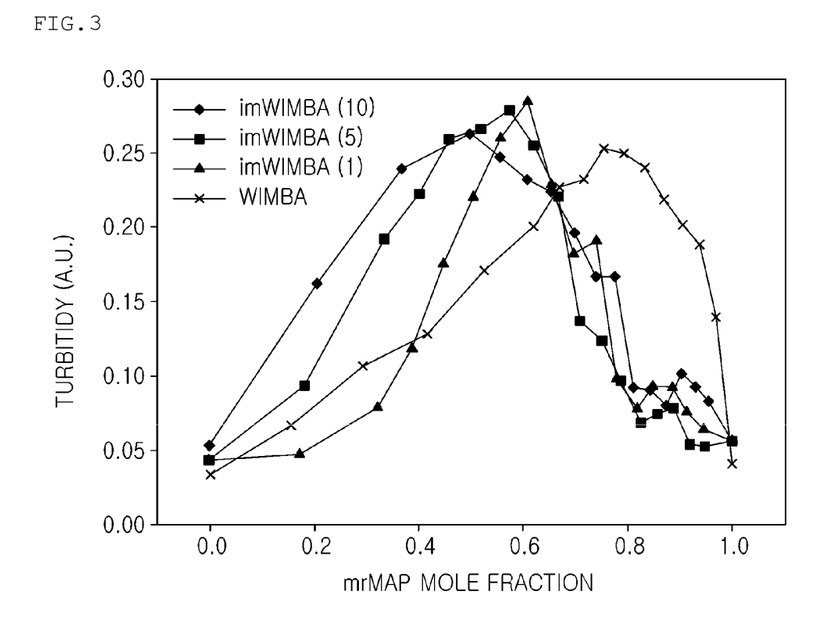
FIG. 3 is a result of UV-Vis spectroscopy analysis confirming that a largest amount of coacervate is formed when the catechol-hyaluronic acid and the mussel adhesive protein are mixed at a particular molar ratio.

In FIG. 3, imWIMBA represents a coacervate using anionic catechol-hyaluronic acid, and numbers in parenthesis represents a molar equivalent of dopamine used in the catechol-hyaluronic reaction. That is, according to FIG. 2, a substitution degree increases as a molar equivalent increases, and this indicates that as the numbers in parenthesis increases, the imWIMBA has a larger amount of catechol. WIMBA represents the coacervate using hyaluronic acid.

The coacervate in the suspension form was centrifuged at 4° C. and 9000 rpm for 10 minutes and then precipitated to obtain a highly coacervate-concentrated phase.

3. Effect of Substitution Degree of Catechol-Hyaluronic Acid on Coacervate

The production of coacervate is affected by a degree of catechol-hyaluronic acid substitution. By varying the substitution degree of catechol-hyaluronic acid, the production of coacervate was observed, and a result thereof is shown in FIG. 4.

Figure 5:
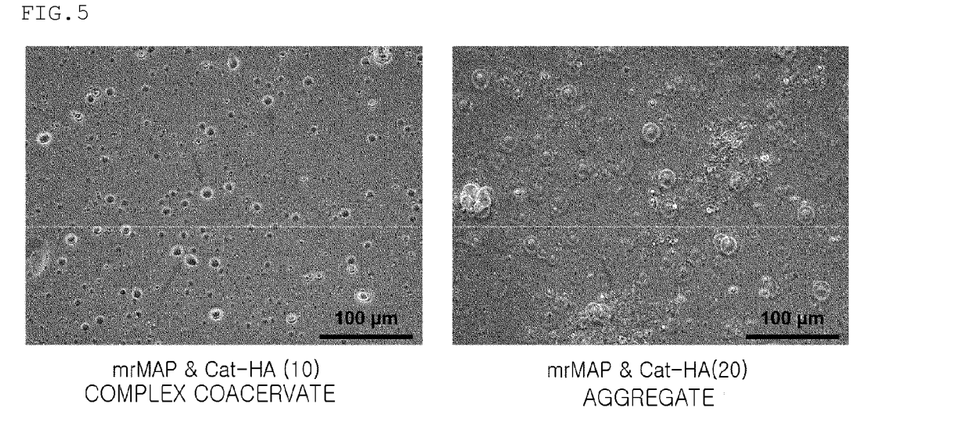
FIG. 5 is a result of observation with an optical microscope confirming that a coacervate or a precipitate is formed when a catechol derivative of a mussel adhesive protein and a catechol-hyaluronic acid having different substitution rates are mixed.

As illustrated in FIGS. 4 and 5, when the substitution degree is 50% or less (left image of FIG. 5) and a molar equivalent of dopamine added to the EDC/NHS reaction for catechol-hyaluronic acid substitution is 10, a coacervate is formed when mixed with the catechol derivative of the mussel adhesive protein. Meanwhile, when the substitution degree is about 75% (right image of FIG. 5) and a molar equivalent of dopamine is 20, anionic residues of the hyaluronic acid, reactive to the cationic mussel adhesive protein, are substituted by dopamine, thereby giving rise to aggregation and subsequent precipitation instead of formation of coacervate. This can be clearly observed by an optical microscope as in FIG. 5.

4. Analysis of Mechanical (Rheological) Properties of Coacervate

To analyze mechanical properties of the coacervate (imWIMBA) produced in 2. above, the catechol was oxidized in a shear stress atmosphere and treated with a crosslinking agent inducing crosslink and measured in terms of storage modulus (G'), loss modulus (G"), complex viscosity, and the like, using a rheometer to measure a crosslinking time required for the crosslink. Sodium periodate having low cellular toxicity was used as the crosslinking agent.

Figure 6:
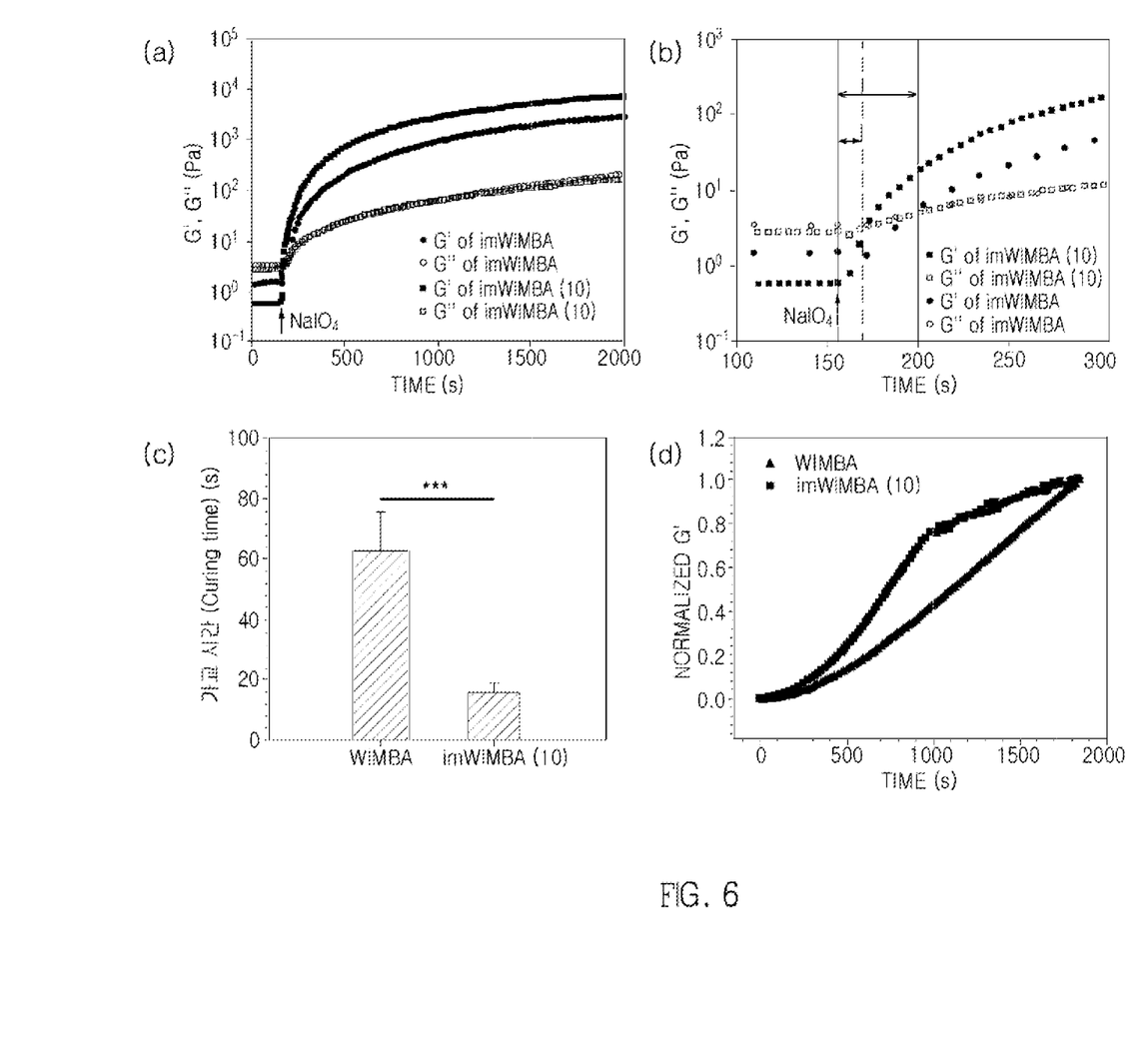
FIG. 6 is diagrams confirming by a rheometer illustrating that mixing a crosslinking agent results in gelation of a liquid coacervate containing a catechol derivative of the catechol-hyaluronic acid/mussel adhesive protein, a coacervate using the catechol-hyaluronic acid is faster than a coacervate using hyaluronic acid at G'=G", a point at which the liquid adhesive can be determined to crosslink with gel, and the coacervate using the catechol-hyaluronic acid reached higher physical properties during a same amount of time.

As illustrated in FIG. 6, the result shows that before the crosslinking agent treatment, G" was observed to be a liquid form having a higher value compared to G'. Upon treatment with the crosslinking agent, however, G' was gradually increased and finally exceeded G", thereby exhibiting gel properties. Crosslinking times of the two coacervates were compared considering a time point at which G' and G" intersect as a crosslinking time, and as a result, the crosslinking time of the coacervate of the present invention was observed to be faster.

Further, in terms of the properties after crosslinking, the coacervate (imWIMBA) of the present invention was higher than the conventional coacervate (WIMBA) using hyaluronic acid, and higher physical properties were reached during the same time.

Based on such properties, the coacervate (imWIMBA) of the present invention was shown to have faster crosslinking and superior properties compared to the conventional coacervate (WIMBA) using hyaluronic acid under the same crosslinking conditions.

5. Measurement of Adhesion Strength and Closing Force of Coacervate

Adhesion strength of the coacervate (imWIMBA) produced in 2. above to a wet oxidized aluminum surface was measured and compared with coacervate (WIMBA) used conventional hyaluronic acid.

Figure 7:
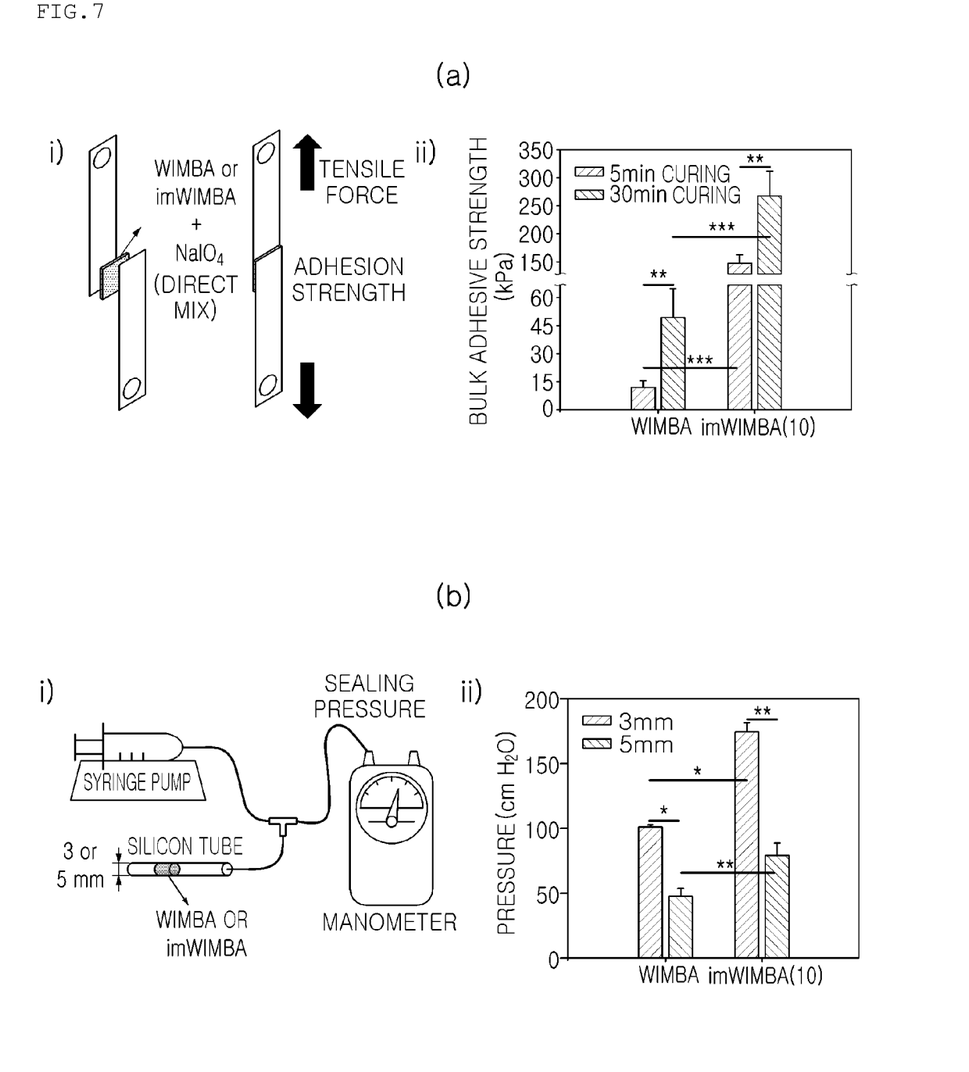
FIG. 7 is a result of comparison of a coacervate containing a catechol-hyaluronic acid with a conventional coacervate in terms of adhesion strength and closing force through a mass adhesion strength test and a silicon tube closing experiment.

As illustrated in FIG. 7, the coacervate (imWIMBA) produced in 2. above was placed on a wet aluminum slice and crosslinked for 5 and 30 minutes in a thermostat and a hygrostat, respectively to measure adhesion strength of the sample. As a result, the coacervate (imWIMBA) of the present invention was shown to have stronger adhesion strength compared to the conventional coacervate (WIMBA) using hyaluronic acid regardless of the crosslinking time. A difference in values of the adhesion strength has statistical significance (FIG. 7A).

Meanwhile, the coacervate (imWIMBA) of the present invention was treated in a silicon tube having a diameter of 3 mm or 5 mm and crosslinked in a thermostat and a hygrostat for about 5 minutes followed by being applied with a constant flow speed to measure pressure the adhesive could withstand. As a result, in addition to the adhesion strength, the coacervate (imWIMBA) of the present invention was shown to have superior closing force than the conventional coacervate (WIMBA) using hyaluronic acid (FIG. 7B).

6. Analysis of Adhesion Strength According to Hyaluronic Substitution Degree

Figure 8:
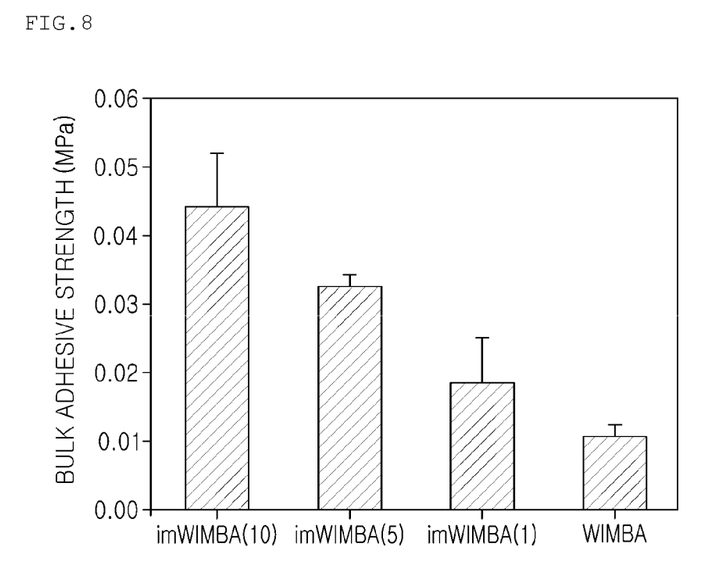
FIG. 8 is a result of an adhesion strength experiment illustrating that as a degree of the catechol-hyaluronic acid substitution increases, a coacervate containing the same shows stronger adhesion strength on wet pig skin.

FIG. 8 illustrates that as an amount of catechol increases, stronger adhesion strength is exhibited to wet pig skin, and confirms that as the substitution degree increases, a total amount of catechol contained in imWIMBA increases.

A crosslinking time was 5 minutes, and the same crosslinking agent used in 4. was used to crosslink in a thermostat and a hygrostat.

As a result, it was shown that compared to an imWIMBA having a low substitution degree, an imWIMBA having a higher substitution degree exhibited higher adhesion strength. Both imWIMBAs were shown to have significantly higher adhesion strength than the WIMBA.

Accordingly, it was confirmed that an addition of catechol to hyaluronic acid would serve to a significantly increased adhesion strength effect.

7. Analysis of Mechanical (Rheological) Properties of Coacervate According to Molecular Weight of Hyaluronic Acid It was measured as to whether mechanical properties of the coacervate produced by varying molecular weights of a mussel adhesive protein and hyaluronic acid forming a mixed coacervate were able to be changed.

Figure 9:
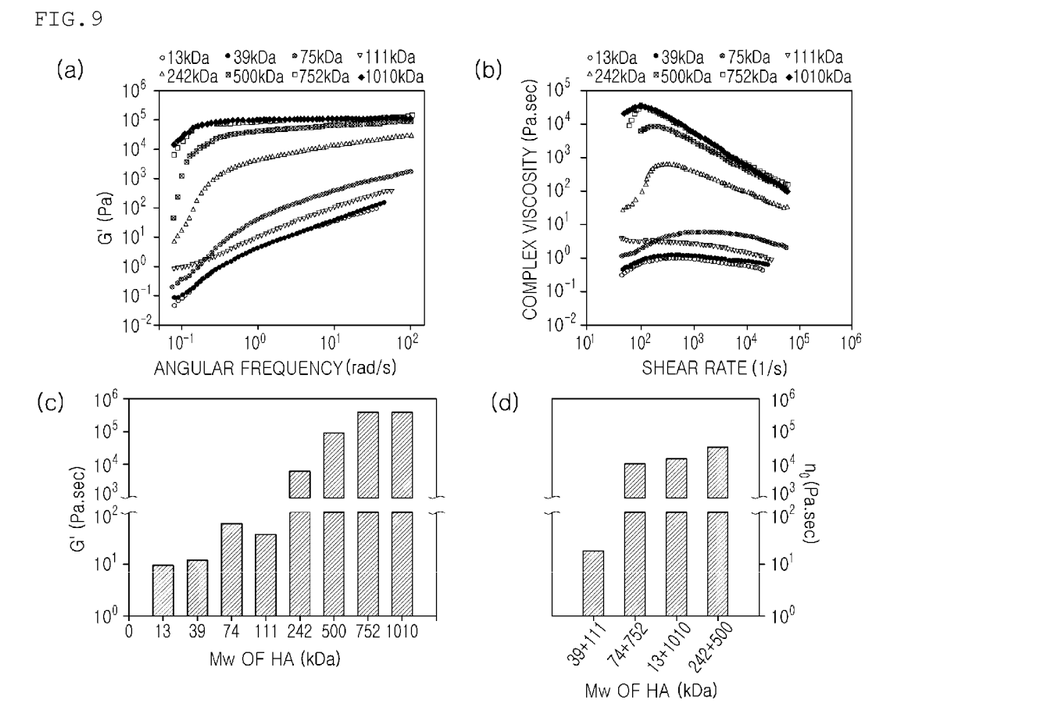
FIG. 9 is a result of measuring mechanical properties and viscosity of a coacervate produced by mixing hyaluronic acids having a variety of molecular weights using a rheometer.

FIG. 9 is a result of measuring mechanical properties and viscosity of a coacervate produced by mixing hyaluronic acids having a variety of molecular weights using a rheometer. As illustrated in FIG. 9, in terms of the coacervate (imWIMBA) of the present invention, the mixed coacervate formed of hyaluronic acids having various molecular weights were shown to have different mechanical properties and viscosity depending on the molecular weights thereof.

When the mixed coacervate is formed of hyaluronic acid of a large molecular weight, the mechanical property and viscosity thereof gradually increased. It was found that the mechanical property and viscosity gradually increased from hyaluronic acid of a low molecular weight to that of a large molecular weight. Further, when a coacervate is produced by mixing hyaluronic acid having various molecular weights, the mechanical property of thus-formed coacervate appears to have an intermediate value of the mechanical properties of the various hyaluronic acid that have been mixed. Based on the above, it is expected that an adhesive having various physical properties can be produced according to uses thereof.

Furthermore, owing to a unique shear thinning property of the coacervate of the present invention, the coacervate formed of hyaluronic acid of a large molecular weight can also be able to be injected through a thin syringe.

Figure 10:
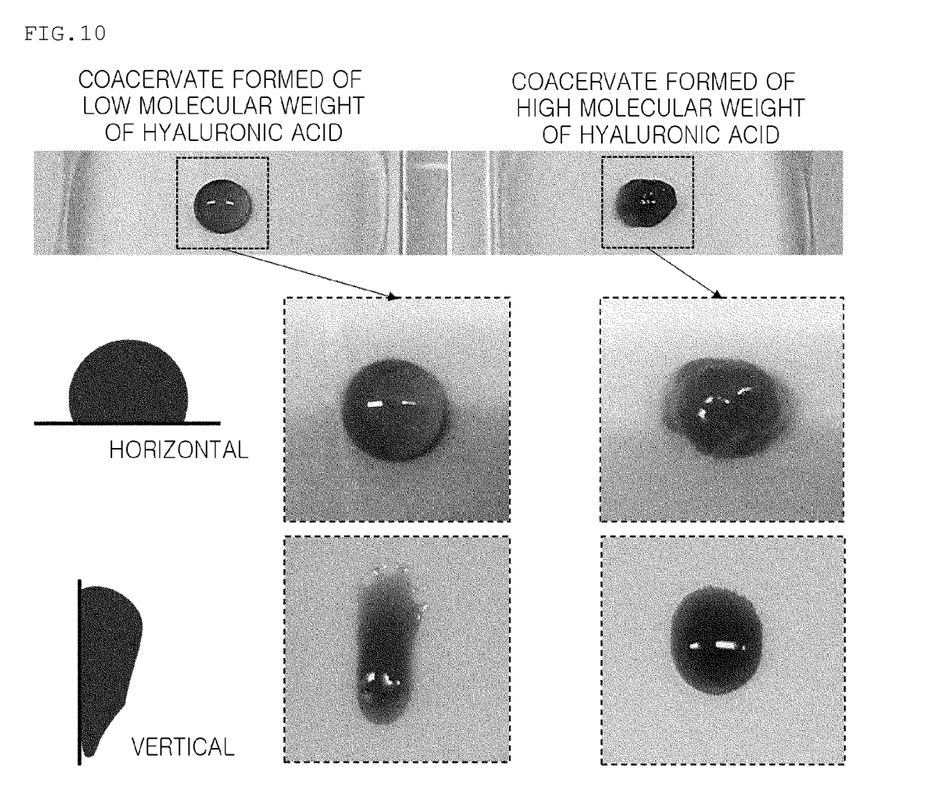
FIG. 10 is a photographic image illustrating a difference in the properties of the coacervate according to molecular weights of the hyaluronic acid.

Meanwhile, it takes a considerable amount of time for the coacervate to be completely adhered to a tissue after being applied as an adhesive and crosslinked. An effect of the adhesive is significantly reduced when the coacervate does not stay in the tissue and flows down due to low physical properties of the coacervate, and this is a problem which can be reduced by shortening the crosslinking time or somewhat guaranteeing the physical properties (or viscosity) of the coacervate itself. Accordingly, for example, when the coacervate formed of hyaluronic acid having a high molecular weight is used, the applied adhesive, as illustrated in FIG. 10, can be prevented from being flown down. In FIG. 10, a low molecular weight was 39 kDa from 13 kDa to 75 kDa, and a high molecular weight was 500 kDa from 111 kDa to 1010 kDa.

However, use of hyaluronic acid of excessively high molecular weights requires a lot of force to be injected due to increased viscosity thereof, which may serve to unpreferable feeling of use. As illustrated in FIG. 9, a coacervate having target viscosity and physical properties may be produced by mixing hyaluronic acid of various molecular weights. This facilitates easy injection and production of a tissue adhesive capable of rapid recover of the physical properties after injection.

While embodiments have been shown and described in detail above, it will be apparent to those skilled in the art that modifications and variations could be made without departing from the scope of the present disclosure as defined by the appended claims.

The invention claimed is:

1. A coacervate comprising:
    a mixture of:
        a catechol derivative of a modified mussel adhesive protein in which a tyrosine residue is modified as a catechol derivative, and
        a catechol-substituted hyaluronic acid as anionic polymer, wherein a substitution degree of the hyaluronic acid is 10% to 52%.

2. The coacervate of claim 1, wherein the catechol derivative of the mussel adhesive protein comprises 10% to 100% of a total number of tyrosine residues the mussel adhesive protein is a catechol derivative substitution.

3. The coacervate of claim 1, wherein the catechol derivative is at least one selected from the group consisting of 3,4-dihydroxyphenylalanine (DOPA), DOPA o-quinone, 2,4,5-trihydroxyphenylalanine (TOPA), TOPA quinone and a derivative thereof.

4. The coacervate of claim 1, wherein a molecular weight of the hyaluronic acid is 1 kDa to 5000 kDa.

5. The coacervate of claim 1, wherein the substitution degree is 30% to 50%.

6. The coacervate of claim 1, wherein the substitution degree is 35% to 50%.

7. An adhesive comprising the coacervate claim 1.

* * * * *